United States Patent
Kielt et al.

(12)

(10) Patent No.: US 7,458,173 B2
(45) Date of Patent: Dec. 2, 2008

(54) ORTHOTIC INSERT AND METHOD OF MANUFACTURE THEREOF

(75) Inventors: Rodney Kielt, Sylvania Waters (AU); Abdul Najjarine, Alfords Point (AU)

(73) Assignee: Foot Steps Orthotics Pty Limited, Miranda New South Wales (AU)

( * ) Notice: Subject to any disclaimer, the term of this patent is extended or adjusted under 35 U.S.C. 154(b) by 326 days.

(21) Appl. No.: 10/501,519

(22) PCT Filed: Jan. 15, 2003

(86) PCT No.: PCT/AU03/00034

§ 371 (c)(1),
(2), (4) Date: Dec. 28, 2004

(87) PCT Pub. No.: WO03/061418

PCT Pub. Date: Jul. 31, 2003

(65) Prior Publication Data

US 2005/0108899 A1    May 26, 2005

(30) Foreign Application Priority Data

Jan. 16, 2002    (AU) .................................... PR9997

(51) Int. Cl.
*A43B 13/38* (2006.01)

(52) U.S. Cl. ................................. 36/44; 36/178; 36/145

(58) Field of Classification Search ..................... 36/43, 36/44, 140, 145, 173, 174, 178–181, 92, 36/71; 12/146 M, 142 N
See application file for complete search history.

(56) References Cited

U.S. PATENT DOCUMENTS

| | | | | |
|---|---|---|---|---|
| 2,255,100 A | * | 9/1941 | Brady | ........................... 36/173 |
| 4,642,911 A | | 2/1987 | Talarico, II | |
| 5,203,793 A | * | 4/1993 | Lyden | ............................ 36/88 |
| 5,542,196 A | | 8/1996 | Kantro | |
| 5,572,805 A | * | 11/1996 | Giese et al. | .................. 36/30 R |
| 5,733,647 A | | 3/1998 | Moore, III et al. | |
| 6,026,599 A | * | 2/2000 | Blackwell et al. | .............. 36/140 |
| 6,061,929 A | * | 5/2000 | Ritter | ........................... 36/107 |
| 6,070,342 A | * | 6/2000 | Brown | ............................ 36/44 |
| 6,233,847 B1 | * | 5/2001 | Brown | ............................ 36/44 |

(Continued)

FOREIGN PATENT DOCUMENTS

GB    2 011 243 A    7/1979

(Continued)

OTHER PUBLICATIONS

Feb. 22, 2005 Supplementary European Search Report for Application No. EP 03 73 1634.

*Primary Examiner*—Marie Patterson
(74) *Attorney, Agent, or Firm*—Nixon Peabody LLP; Jeffrey L. Costellia

(57) ABSTRACT

An orthotic insert (1) having a first (2) and second portion (3), the second portion being formed of a material of higher resistance to deformation than the first portion (2), wherein the insert (1) is heat mouldable to conform to a patient's foot. The first portion (2), which forms the main body of the insert (1) provides support for the fore foot, while the second portion (3) is substantially U or J-shaped and extends around the heel region and into the arch region of the patient's foot. Preferably both portions are formed from heat mouldable ethyl vinyl acetate.

9 Claims, 7 Drawing Sheets

U.S. PATENT DOCUMENTS

| | | | |
|---|---|---|---|
| 6,247,250 B1 * | 6/2001 | Hauser | 36/44 |
| 6,286,232 B1 * | 9/2001 | Snyder et al. | 36/43 |
| 2002/0050080 A1 * | 5/2002 | Vasyli | 36/145 |
| 2002/0056208 A1 * | 5/2002 | Brown | 36/44 |
| 2002/0083618 A1 * | 7/2002 | Erickson et al. | 36/44 |
| 2003/0005599 A1 * | 1/2003 | Panaccione | 36/43 |
| 2003/0033733 A1 * | 2/2003 | Brooks | 36/31 |
| 2003/0182821 A1 * | 10/2003 | Chen | 36/92 |

FOREIGN PATENT DOCUMENTS

| | | |
|---|---|---|
| NZ | 196010 | 1/1982 |
| WO | WO 91/07152 | 5/1991 |
| WO | WO 92/19191 | 11/1992 |

* cited by examiner

ORTHOTIC INSERT AND METHOD OF MANUFACTURE THEREOF

FIELD OF THE INVENTION

This invention relates to orthotic inserts and to a method of manufacturing orthotic inserts.

BACKGROUND ART

Any discussion of the prior art throughout the specification should in no way be considered as an admission that such prior art is widely known or forms part of common general knowledge in the field.

The human foot is a complex structure made up of 28 bones held together by soft tissue, muscles, ligaments and tendons.

Orthotic inserts are used to provide additional support for the feet of a wearer, particularly in circumstances where the wearer requires a degree of bio-mechanical support and control.

Orthotic inserts can range from simple foam, leather, cork, or sponge rubber arch supports that can be purchased over the counter, through to relatively sophisticated custom made inserts. Typically, the more sophisticated orthotic inserts are relatively expensive and are produced on a custom made basis in accordance with detailed prescriptions provided by the examining doctor.

The primary function of an orthotic insert is to control any excessive pronation and supination that a person may experience as his or her foot strikes the ground during walking or running. Pronation is the flattening or rolling inward of the foot as the foot strikes the ground, whilst supination is the rolling outward of the foot during walking or running. If either of these motions become excessive, damage to the knees, ankles and feet can occur.

Known orthotic inserts rely upon the contouring of the upper surface of the insert to provide the necessary degree of support and control for the wearer. However, in certain circumstances this may not provide sufficient comfort for the wearer.

It is therefore an object of the present invention to overcome or ameliorate at least one of the disadvantages of the prior art, or to provide a useful alternative.

SUMMARY OF THE INVENTION

To this end, a first aspect of the present invention provides a heat mouldable orthotic insert having a first and second portion, wherein said second portion is formed of a material of higher resistance to deformation than said first portion.

Preferably, both the first and second portions of the orthotic insert are formed from resilient material, with the second portion being formed from a resilient material of higher resistance to deformation than said first portion.

Preferably, the second portion is formed from a material of higher density than the material from which the first portion is made.

Preferably, said first and second portions of the orthotic insert are formed from heat mouldable ethyl vinyl acetate.

Preferably, said first and second portions of the orthotic insert are joined by bonding. More preferably, said first and second portions are joined together by gluing.

Preferably, the second portion is adapted to provide support for the heel region of a person's foot. In a further preferred embodiment, the second portion is adapted to provide support for the heel and arch regions of a person's foot.

In one particularly preferred embodiment, the second portion has a substantially U- or J-shaped configuration which extends partially around the periphery of the insert corresponding to the heel and arch regions of a person's foot.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

Advantageously, the orthotic insert according to the present invention is able to be heat moulded to the contours of the underside of a person's foot in the correct biomechanical position whilst standing in a weight bearing position.

Advantageously, in one particularly preferred embodiment the present invention provides an orthotic insert which provides improved support and comfort for a person's foot around the heel and arch areas.

A second aspect of the present invention provides a method of producing an orthotic insert comprising forming a first portion of the insert, forming a second portion of the insert from a material of higher resistance to deformation than said first portion of the insert, and joining said first and second portions together to form the insert.

Preferably, the first portion of the insert is formed by moulding. More preferably, the first portion of the insert is formed by heat moulding.

Preferably, the second portion of the insert is formed by moulding. More preferably, the second portion of the insert is formed by heat moulding.

Preferably, the said first and second portions are joined together by means of bonding. More preferably, the first and second portions are joined together by gluing.

In one particularly preferred embodiment, the second portion has a substantially U- or J-shaped configuration which extends partially around the periphery of the insert corresponding to the heel and arch regions of a person's foot.

BRIEF DESCRIPTION OF THE DRAWINGS

Preferred embodiments of the invention will now be described, by way of example only, with reference to the accompanying drawings in which.

DETAILED DESCRIPTION OF THE PREFERRED EMBODIMENT

Figure 1:
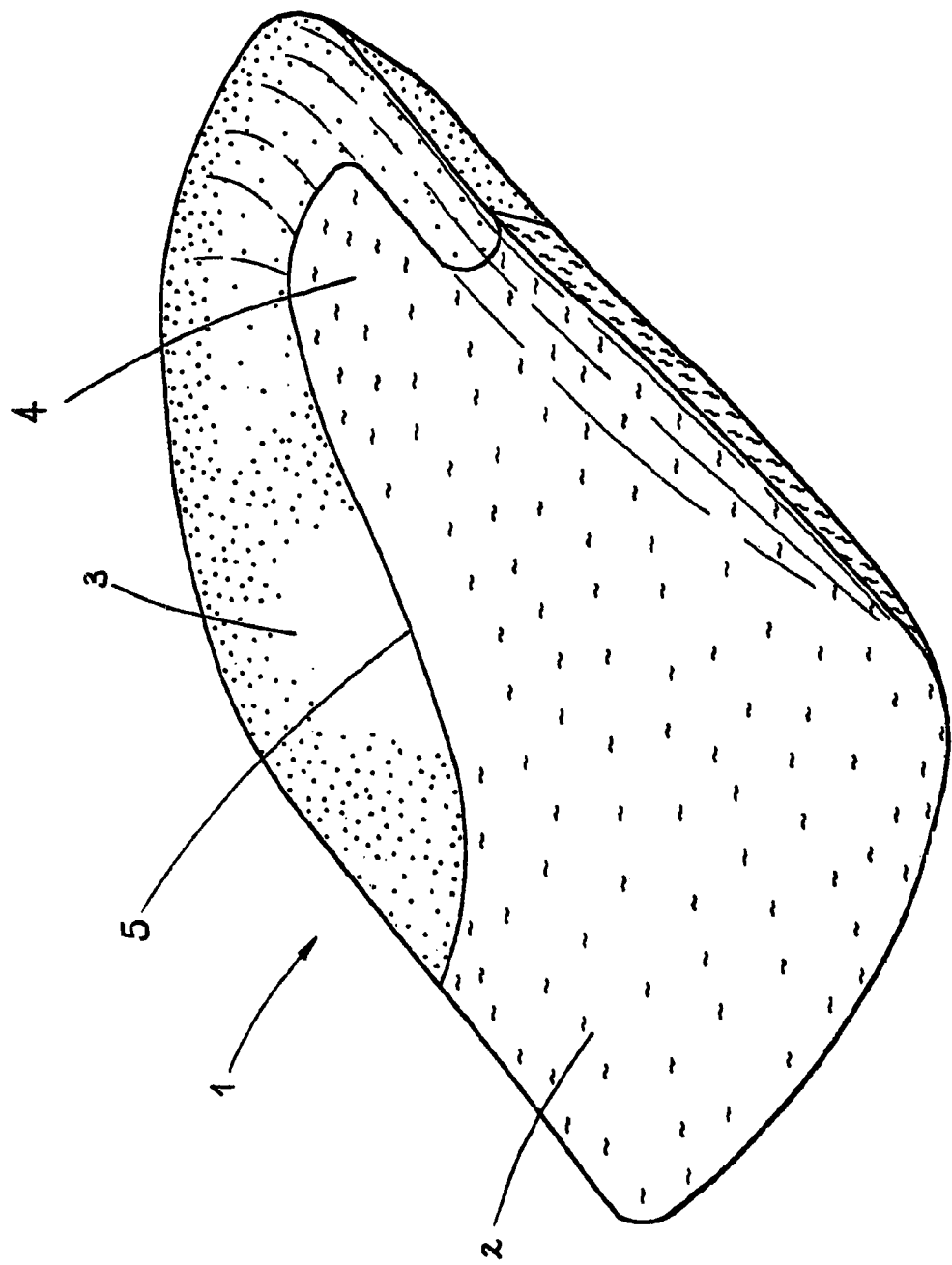
FIG. 1 is a perspective view of one embodiment of an orthotic insert according to the present invention.
Figure 2:
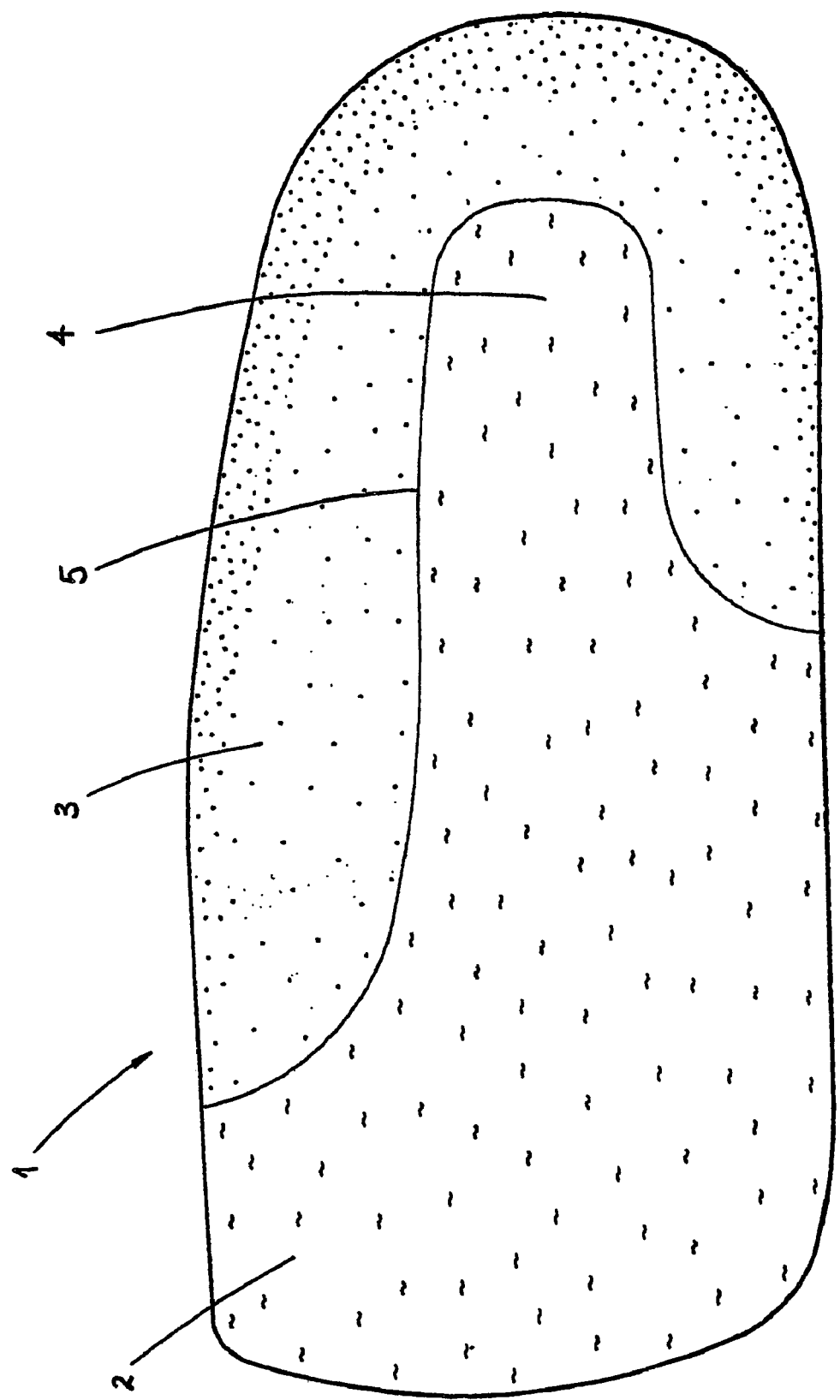
FIG. 2 is a plan view of the orthotic insert depicted in FIG. 1.
Figure 3:
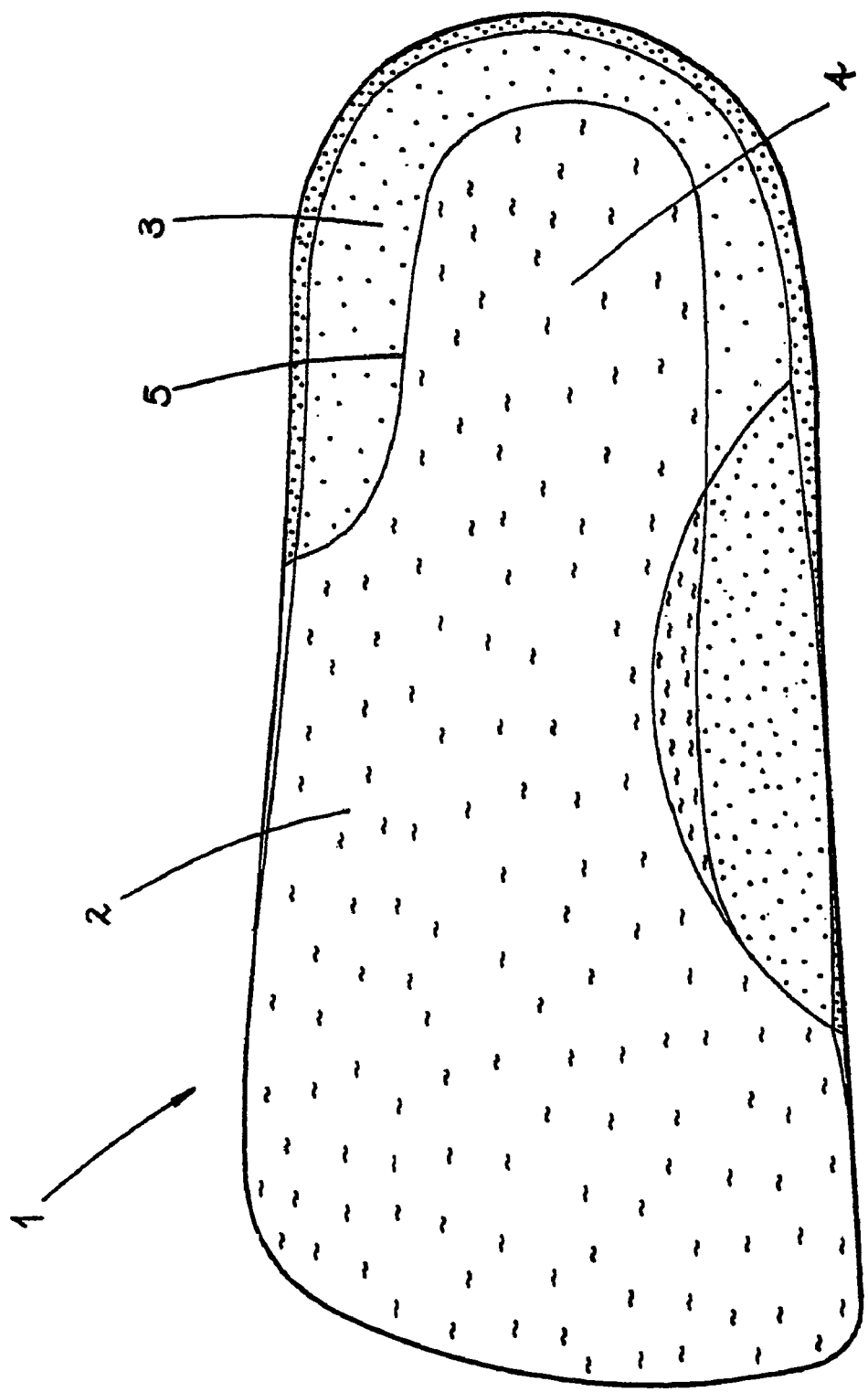
FIG. 3 is an underside view of the orthotic insert depicted in FIG. 1.
Figure 4:
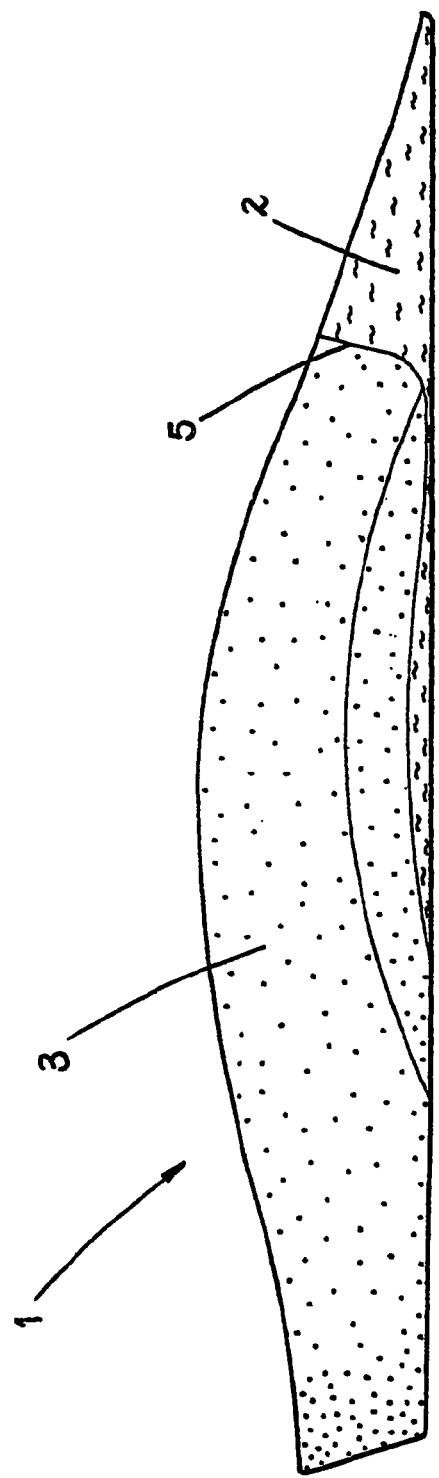
FIG. 4 is a left hand view of the orthotic insert depicted in FIG. 1.
Figure 5:
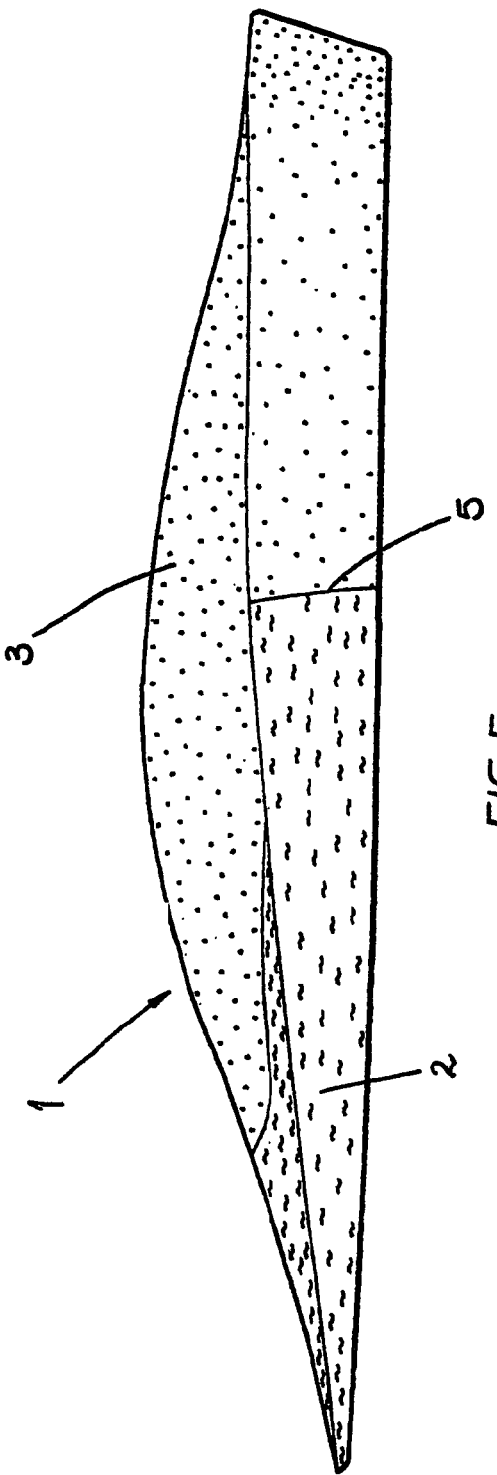
FIG. 5 is a right hand view of the orthotic insert depicted in FIG. 1.
Figure 6:
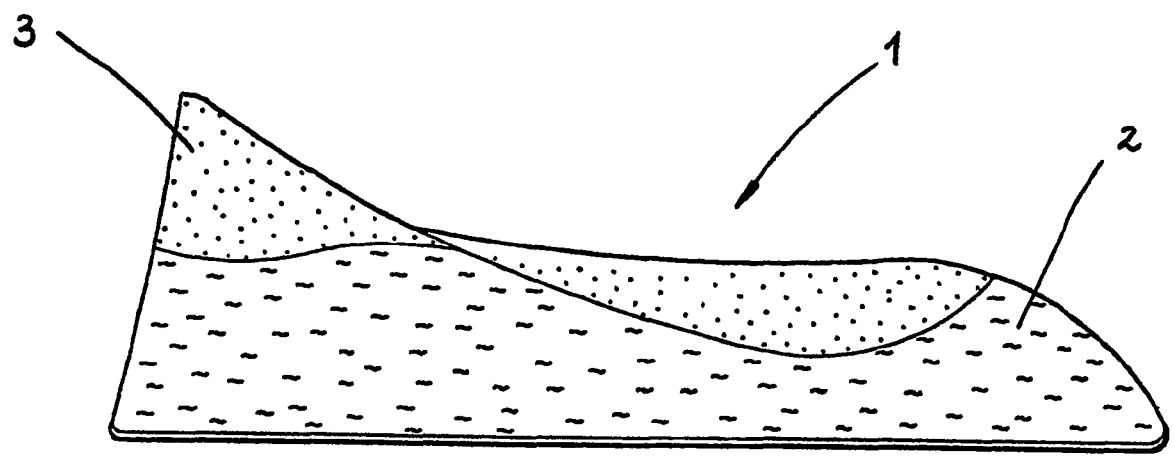
FIG. 6 is a front view of the orthotic insert depicted in FIG. 1.
Figure 7:
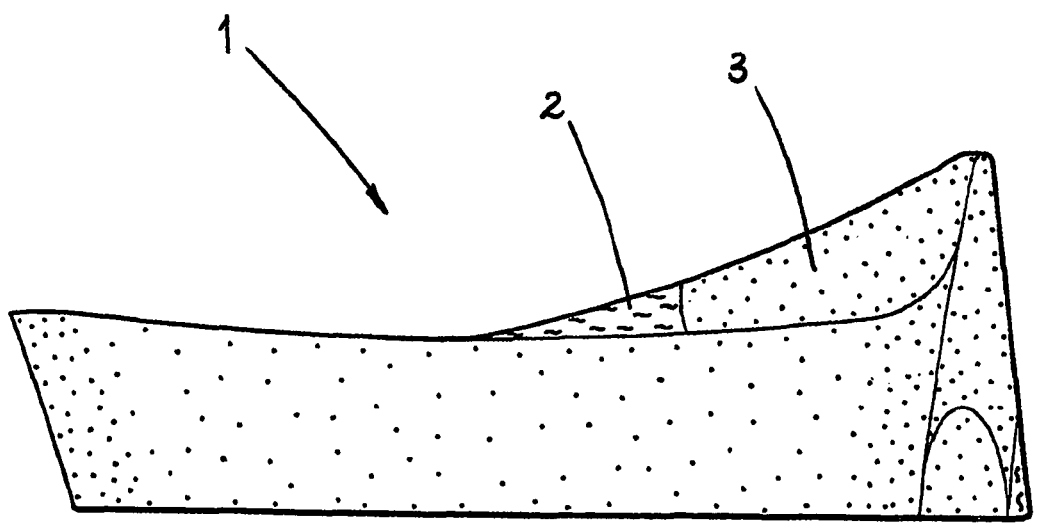
FIG. 7 is a rear view of the orthotic insert depicted in FIG. 1.

Referring to FIGS. 1 to 7, a preferred embodiment of an orthotic insert 1 according to the present invention is depicted. The orthotic insert depicted is for the left foot of a person and is adapted to be inserted into an article of footwear such that in use the insert lies between the footwear and the underside of the person's foot so as to provide a degree of biomechanical support and control for the foot. The orthotic insert depicted in the accompanying drawings is a three-quarter length insert, but it should be noted that the present invention is applicable to all lengths of orthotic inserts, such as full length inserts.

In accordance with one aspect of the present invention, the orthotic insert is formed from portions 2, 3 of differing resistance to deformation. More particularly, in the preferred embodiment of the invention, the region of the orthotic insert surrounding the heel of the wearer comprises a portion 3 formed from a material which is more resistant to compression than the portion 2 which forms the remainder of the body of the insert. Typically, the portion 3 is between 30 to 70% more resistant to deformation than the portion 2. More typically, the portion 3 is between 40 to 60% more resistant to deformation than portion 2.

The first portion 2 of the orthotic insert forms the main body of the insert and provides support for the fore foot. This portion of the orthotic insert may include an integrally formed metatarsal raise.

The second portion 3 of the orthotic is located in the heel region of the insert. In the embodiment depicted in FIGS. 1 to 7, the second portion 3 has a substantially U or J-shaped configuration which extends around the heel region and into the arch region of the wearer's foot. The first portion 2 includes a tongue 4 which is located within a complementary shaped recess in the second portion. In use the tongue 4 lies beneath the calcaneus of the wearer. The first and second portions of the insert are joined together by bonding along the interface 5.

In a preferred embodiment the first portion of the orthotic is formed from heat mouldable ethyl vinyl acetate.

Preferably the second portion of the insert is formed from heat mouldable ethyl vinyl acetate of a higher density than that of the first portion such that it has a higher resistance to compression thereby providing firmer support in the heel and arch areas of the foot of the wearer. This preferred embodiment offers rear foot and arch control from a higher density EVA material, combined with the comfort of a softer mid-density EVA, resulting in comfort and control in the gait cycle from heel strike, midstance to toe off, whilst maintaining medial and rear foot control throughout.

Figure 8:
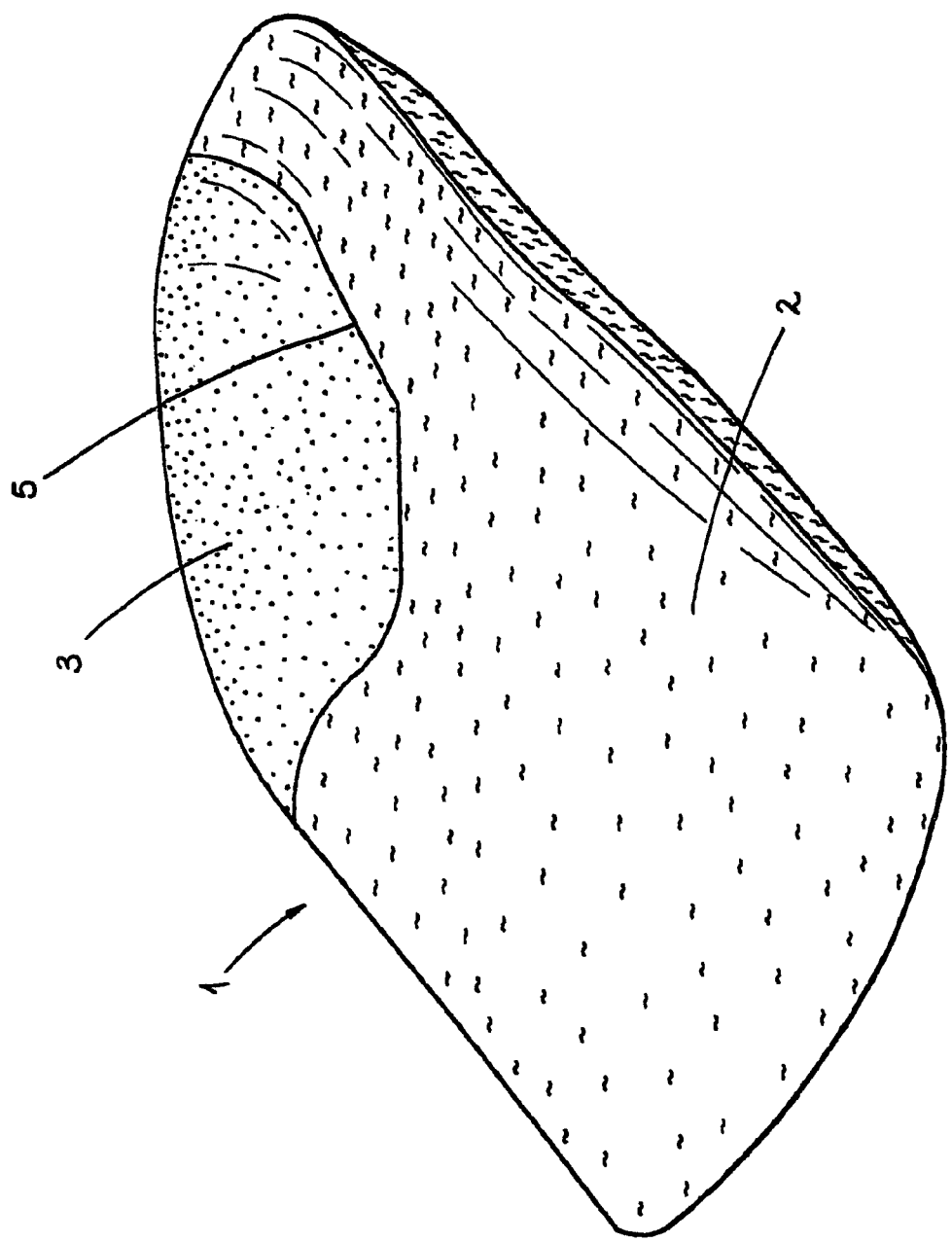
FIG. 8 is a perspective view of an alternative embodiment of an orthotic insert according to the present invention.
Figure 9:
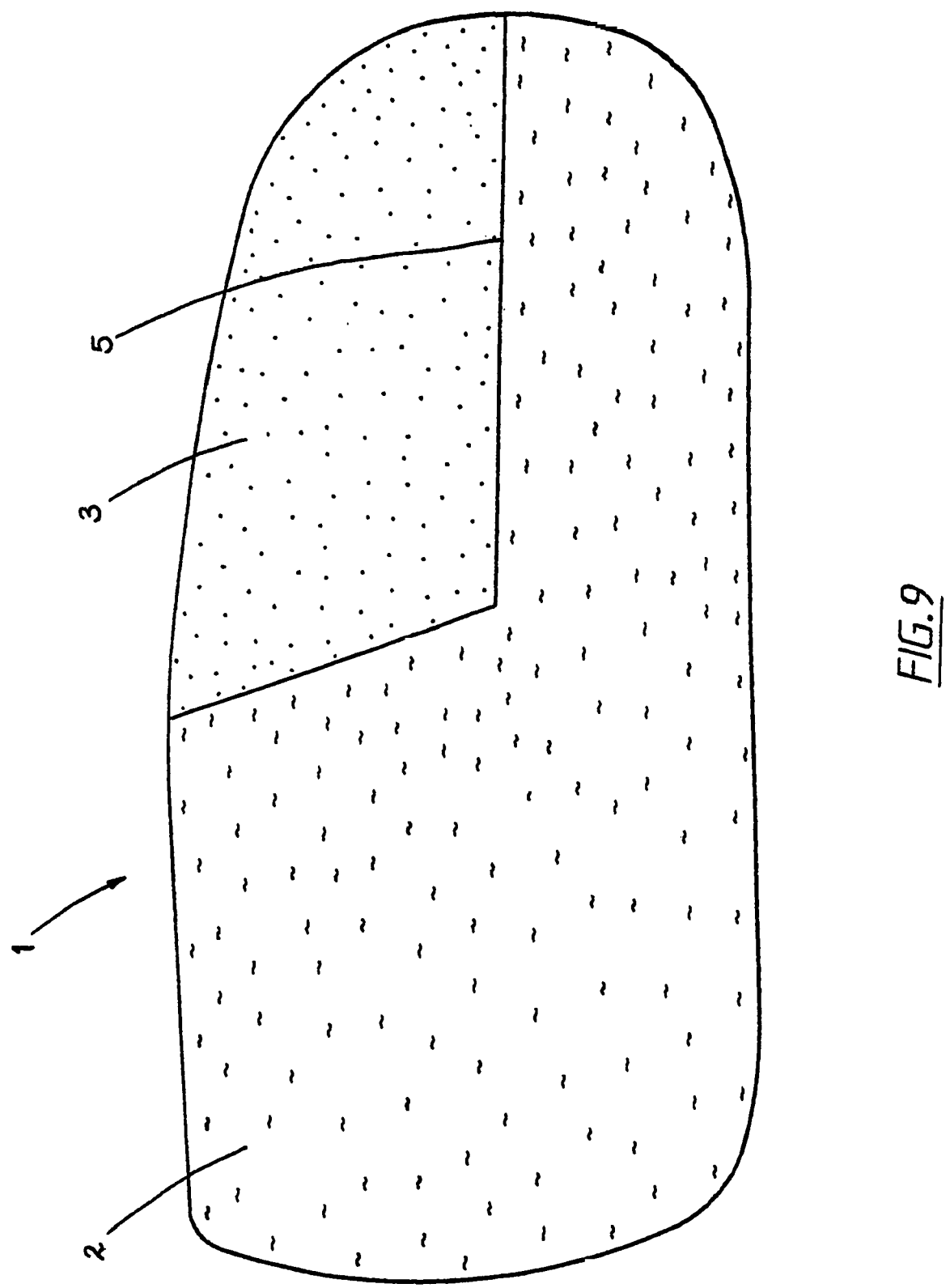
FIG. 9 is a plan view of the orthotic insert depicted in FIG. 8.

Whilst the preferred embodiment depicted in FIGS. 1 to 7 illustrates a second portion 3 having a substantially U- or J-shaped configuration, it is to be noted that the portion of firmer material may be configured in differing shapes according to the orthotic requirements of the intended wearer. Additionally, the portion of firmer material may be located at different locations on the insert depending upon the requirements of the intended wearer. For example, an alternative embodiment of an orthotic insert according to the present invention is depicted in FIGS. 8 and 9. In this embodiment, the insert includes a portion of firmer material 3 which forms approximately one half of the heel section of the insert such that the interface 5 between the two portions 2, 3 defines a longitudinally extending line. In this embodiment, portion 3 provides additional support for the inside of the heel of the wearer.

Additionally, it is to be noted that the orthotic may be formed from a multitude of separate portions joined together to form the complete insert. Each portion may be formed of materials of differing properties so as to provide the desired degree of support for particular regions of the person's foot. For example, the insert may be formed of three or more separate portions of differing material properties joined together to form the complete insert.

In the preferred embodiment of the invention both the first and second portions of the orthotic insert are formed from heat mouldable ethyl vinyl acetate of differing densities. However, it should be noted that each portion of the orthotic insert could be formed from distinctly different materials.

In order to manufacture the orthotic insert each portion of the insert is cut to a basic shape and then placed into a mould. The mould is subsequently put under pressure and heated to a temperature of the order of 140° C. The moulds are then left for a period to cool down and then the portions are extracted and trimmed to their desired shapes. The two portions are then glued together using an aqueous based heat resistant glue so as to form the completed insert. The orthotic insert is then fitted to the foot of the intended wearer by means of heat moulding.

In order to fit orthotic inserts according to the present invention to a patient, inserts of the appropriate size and material density for the patient are selected. An insert is then heated until the insert material softens. Heating of the insert may be performed by a number of possible means, including a hot air gun or by placing the insert in an oven. The heated insert is then placed into the shoe of the patient and the patients foot is placed into the shoe in the subtalar neutral position. The pressure exerted on the heated insert by the weight of the patient causes the upper surface of the insert to conform to the patient's foot. Typically the patient must maintain the position for a short period (i.e. 30 seconds to a minute) to allow sufficient time for the insert to conform. Upon cooling the insert will retain the shape to which it has conformed. This process is then repeated for the other foot of the patient.

Advantageously, the present invention provides a prefabricated orthotic insert that can be heat moulded to a particular foot in the correct biomechanical position whilst standing in a weight bearing position. This contrasts with custom fitted orthotic inserts which typically require the profile of the person's foot to be scanned so as to enable a blank orthotic to be milled to provide the correct profile.

Although the invention has been described with reference to specific examples it will be appreciated by those skilled in the art that the invention may be embodied in many other forms.

The claims defining the invention are as follows:

1. An orthotic insert having a first and a second portion, said first and second portions being formed from heat mouldable ethyl vinyl acetate, said second portion adapted to provide support in the heel region of a person's foot and being formed of a material of higher resistance to deformation than said first portion, wherein said insert is heat mouldable to conform to the person's foot such that to fit said insert to person's foot said insert is heated until it softens sufficiently to permit an upper supporting surface of the insert to conform to said patient's foot to provide the desired biomechanical support and then subsequently cooled, where upon cooling said upper supporting surface of said insert retains the shape to which is has conformed, and the second portion has a substantially J-shaped configuration which extends partially around the periphery of the insert corresponding to the heal and arch regions of the person's foot and a lateral section of the second portion extends above said upper supporting surface of the first portion to support the arch region of the person's foot.

2. The orthotic insert as claimed in claim 1, wherein the second portion is formed from a material of higher density than the material from which the first portion is formed.

3. The orthotic insert as claimed in claim 1, wherein said first and second portions of the orthotic insert are joined by bonding.

4. The orthotic insert as claimed in claim 1, wherein the second portion is adapted to provide support for the heel and arch regions of a person's foot.

5. The orthotic insert as claimed in claim 1, wherein said first portion includes an integrally formed metatarsal raise.

6. The orthotic insert as claimed in claim 1, wherein said first portion includes a tongue which is located within a complementary shaped recess in the second portion.

7. The orthotic insert as claimed in claim 6, wherein said tongue lies beneath the calcaneus of the patient.

8. The orthotic insert as claimed in claim 1, wherein said second portion is between 30 to 70% more resistant to deformation than said first portion.

9. The orthotic insert as claimed in claim 1, wherein said second portion is between 40 to 60% more resistant to deformation than said first portion.

* * * * *